US008619946B2

(12) United States Patent
Hanke et al.

(10) Patent No.: US 8,619,946 B2
(45) Date of Patent: Dec. 31, 2013

(54) X-RAY SOURCE AND X-RAY SYSTEM

(75) Inventors: Wilhelm Hanke, Rückersdorf (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 271 days.

(21) Appl. No.: 13/054,371

(22) PCT Filed: Jun. 9, 2009

(86) PCT No.: PCT/EP2009/057085
§ 371 (c)(1), (2), (4) Date: Jan. 14, 2011

(87) PCT Pub. No.: WO2010/006846
PCT Pub. Date: Jan. 21, 2010

(65) Prior Publication Data

US 2011/0122992 A1 May 26, 2011

(30) Foreign Application Priority Data

Jul. 15, 2008 (DE) ........................ 10 2008 033 150

(51) Int. Cl.

| | |
|---|---|
| ***A61B 6/04*** | (2006.01) |
| ***H01J 35/10*** | (2006.01) |
| ***G01N 23/04*** | (2006.01) |

(52) U.S. Cl.
USPC ................................ 378/124; 378/37; 378/62

(58) Field of Classification Search
USPC .............. 378/37, 62, 124, 136, 138, 143, 144
See application file for complete search history.

(56) References Cited

U.S. PATENT DOCUMENTS

| | | | |
|---|---|---|---|
| 4,433,431 | A | 2/1984 | Pfeiler |
| 5,142,652 | A | 8/1992 | Reichenberger et al. |
| 5,383,232 | A | 1/1995 | Gabbay et al. |
| 3,229,089 | A | 1/1996 | Saburo Sasao |
| 7,433,444 | B2 | 10/2008 | Baumann et al. |
| 2005/0100126 | A1 | 5/2005 | Mistretta et al. |
| 2006/0182223 | A1 | 8/2006 | Heuscher |
| 2010/0074392 | A1 | 3/2010 | Behling et al. |

FOREIGN PATENT DOCUMENTS

| | | |
|---|---|---|
| DE | 103 56 601 A1 | 7/2005 |
| JP | 2007323964 | 12/2007 |

OTHER PUBLICATIONS

"A Multi-Beam X-ray Imaging System Based on Carbon Nanotube Field Emitters," Zhang et al., Medical Imaging, vol. 6142, 614204-1 (2006).

*Primary Examiner* — Irakli Kiknadze
(74) *Attorney, Agent, or Firm* — Schiff Hardin LLP

(57) ABSTRACT

An x-ray source has multiple electron sources spaced apart from each other along a longitudinal direction that is defined as being parallel to the rotation axis of a rotating anode which is common to all of the electron sources. Each electron source emits electrons that strike the anode at respective strike points that are spatially separated from each other along the longitudinal direction, to produce respective emission centers, from which x-rays are emitted, each emission center being associated with respective ones of the x-ray sources.

13 Claims, 4 Drawing Sheets

X-RAY SOURCE AND X-RAY SYSTEM

BACKGROUND OF THE INVENTION

1. Field of the Invention

The invention concerns an x-ray source of the type having multiple of electron sources separated from one another in a longitudinal direction, as well as an x-ray system with such an x-ray source.

2. Description of the Prior Art

Tomographic imaging x-ray methods (as are used for non-destructive materials testing, for example, but in particular in medicine) expose the examination subject to radiation from different directions. The individual projections obtained in this manner are subsequently calculated into a spatial image of the examination subject. The exposure of the examination subject from different directions is achieved by a movement of the x-ray source. For example, in computed tomography (CT) of the patient that is used in medicine, the patient is irradiated by an x-ray source rotating around the patient. Tomosynthesis is a further medical examination method with which a spatial image of the examination subject (in this case of the breast) can be acquired. In this special form of mammography, the breast is irradiated from directions situated in a limited angle range. In tomosynthesis the x-ray source is also moved relative to the examination subject.

However, movement of the x-ray source always entails technical problems. For example, given fast movement high inertial forces occur that the mechanical construction of the x-ray source must withstand. The x-ray source must typically be supplied with electrical power and cold water; both supply lines must follow the movement of the x-ray source or be strengthened so as to permit movement of the x-ray source by appropriate measures that are technically complicated, for example slip contacts or rotary transmission leadthroughs.

In order to avoid the need for movement of the x-ray source, the use of a stationary x-ray source having multiple of x-ray emitters (also designated as emitters for short) is proposed by J. Zhang et al. in "A multi-beam x-ray imaging system based on carbon nanotube field emitters", Medical Imaging, Vol. 6142, 614204 (2006). The acquisition of tomographic image data sets is possible with such an x-ray source (also designated as a multifocus x-ray source) without a mechanical movement of the x-ray source being required. The examination subject is exposed with x-ray beams from different directions by the individual emitters of the multifocus x-ray source are excited to emission in chronological succession. In the course of an examination, the individual emitters are excited (activated) sequentially or even simultaneously to output an x-ray dose. If a detector that can be read out quickly is used in such a system, short scan times are possible.

In order to enable x-ray exposures with high resolution with short scan time of the examination subject, x-ray sources with high power are required. However, the power of known multifocus x-ray sources is limited by their thermal loading capacity. If this is exceeded, melting of the anode surface can occur. In order to avoid this and other consequences of thermal overloading, in conventional x-ray sources only low x-ray powers can be required by the individual emitters. Conventional multifocus x-ray sources are therefore limited to low amperages and short emission times.

SUMMARY OF THE INVENTION

An object of the present invention is to provide an x-ray source and an x-ray system with such an x-ray source that is suited to emit multiple x-ray beams and is improved with regard to its x-ray power.

The x-ray source according to the invention has a number of electron sources that are spaced apart from one another in a longitudinal direction and a common anode that is arranged opposite these electron sources and likewise extends in the longitudinal direction. The electrons emanating from the electron sources strike points on the anode that are spatially separated from one another and in this way generate separate emission centers that are respectively associated with an electron source. The anode of the x-ray source can be rotated around an axis oriented in the longitudinal direction.

In an x-ray source with these features, the electrons striking the anode generate emission centers on the anode at locations that are spatially separated from one another. In this way it is possible to optimally construct an x-ray source that is suitable for the emission of multiple x-ray beams but has only one anode. In order to counteract the thermal problems that typically occur in multifocus x-ray tubes, the common anode is designed so that it can rotate. Instead of a focal spot, the electron beam striking the anode rotating in the operation of the x-ray source generates a focal spot path that extends along the perimeter of the anode. In comparison to the focal spot generated on a stationary anode, the area of this focal spot path is significantly larger. The volume of the anode that is heated by the impinging electrons is correspondingly greater. The thermal power introduced into the anode material is thus distributed in a greater volume. Since more anode material with a comparably larger surface is heated relative to a conventional x-ray source with a stationary anode, a more effective radiation of its thermal energy can take place. The x-ray source according to the invention therefore has a higher thermal loading capability. This has a particularly positive effect in an x-ray source that has a plurality of emission centers.

The rotation axis of the anode extends in the longitudinal direction of the x-ray source. The electron sources that are spaced apart from one another are likewise arranged along this longitudinal direction. The electrons emanating from the electron sources cause emission centers on one and the same anode that are spatially spaced apart from one another in the longitudinal direction. This geometry allows an x-ray source with separate emission centers to be realized and simultaneously allows the use of a rotating anode. The x-ray source advantageously has a very simple mechanical design since only one common anode with a single rotation axis can be used to generate the separate emission centers.

According to a first embodiment, the anode is a rotation body; this is cylindrical. The anode typically rotates with a high frequency during the operation of the x-ray source. In that the anode is designed as a rotation body, it can advantageously be avoided that this exhibits an out-of-balance. Moreover, rotation bodies are often simple to produce and are very robust with regard to centrifugal forces (inertial forces) that occur.

The anode of the x-ray source is exposed to varying stresses. As mentioned large centrifugal forces act on the anode material; on the other hand, the anode is severely heated by the incident electrons. Not least, in the region of the focal spot path the anode must consist of the material that matches the desired x-ray emission.

The material that causes a desired x-ray emission is also designated in the following as anode material. Tungsten is such an anode material, for example. The bremsstrahlung spectrum, including the material-specific and characteristic x-ray lines, is normally used as an x-ray emission. The low-energy portions of the bremsstrahlung spectrum can be filtered out via the use of corresponding filters.

As was already addressed, an anode should now fulfill as many requirements as possible. In particular, this should be mechanically loadable and deliver the desired x-ray emissions. According to a further embodiment, the x-ray source is improved in that its anode is a composite anode made up of a base body and a cover layer which serves as an anode material. The base body and the cover layer exhibit different material compositions. The design and the selected material compositions of such a composite anode can be flexibly adapted to the occurring loads. The cover layer advantageously occupies at least one partial region of the surface shell of the anode. This partial region will likewise preferably extend along the perimeter of the anode. Naturally, it is also possible to provide the entire surface shell of the anode with a cover layer.

According to a further embodiment, the cover layer extends along the perimeter of the anode in the form of segments that are spatially spaced apart from one another in the longitudinal direction. The individual segments of the cover layer are respectively associated with an emission center, meaning that a focal spot path that is generated by the electron beam of an electron source is respectively located on a segment. The anode material of the cover layer is normally more expensive than that material which can be used for the base body of the anode. An economical handling with the anode material of the cover layer is therefore suggested. In that this is brought onto or into the base body in the form of advantageously annular segments, only as much anode material is used as is necessary to generate the desired x-ray emission. Similar demands as in conventional rotating anodes are made of the base material. It is typically required of the base material that this possesses a high heat capacity and a good heat conductivity so that the heat that is introduced into the anode material can be reliably dissipated. In contrast to this, the anode is predominantly selected with regard to the desired x-ray emission. The anode material typically possesses a high melting point so that high x-ray emission powers can be achieved.

Depending on the use of the x-ray source, varying wavelengths or wavelength ranges are used as x-ray emissions. A change of the x-ray emissions typically occurs via an exchange of the anode material. In conventional x-ray apparatuses, the entire x-ray source is exchanged multiple times for this purpose, which represents a significant expense. According to one embodiment, this modification cost is superfluous due to the use of an x-ray source since this already comprises two different anode materials for the emission of two different x-ray emissions. Such an x-ray source possesses an anode with a cover layer that is subdivided into segments of a first segment group and into segments of a second segment group. A segment of the first segment group and a segment of the second segment group are respectively arranged next to one another in pairs in the longitudinal direction. The segments of the first segment group and the segments of the second segment group possess a different material composition. This means that the segments are arranged in pairs on the anode, wherein a segment of the first segment group and a segment of the second segment group are respectively assembled into one pair. The segments are arranged such that segments of different segment groups are respectively arranged directly adjacent to one another.

With an x-ray source according to the preceding embodiment it is possible to use the x-ray emissions of two different materials without a change of the x-ray source even having to be implemented. The electron beam is selectively directed onto the segment of the first segment group or the segment of the second segment group depending on which x-ray emission is desired.

The change of the anode material can be produced both via a displacement of the electron beam and via a displacement of the anode. Since the segments of a pair are spaced out among one another in the longitudinal direction, such a displacement takes place in the longitudinal direction.

According to a further embodiment, at least one x-ray source is designed such that the electrons emanating from it strike the anode on the surface in such a direction that is different from its surface perpendiculars at the impact point of the electrons. In other words, the electron beam emanating from the electron source—considered in a plane that contains the rotation axis of the anode and is oriented essentially perpendicular to the radiation direction of the electron beam—strikes the anode in a region between its edge and its rotation axis. Due to the excitation of the anode material in such an eccentrically placed region, the arising x-ray radiation has a short path through the anode material, which advantageously only insignificantly attenuates this radiation.

According to one embodiment, for a more effective excitation of the anode material of the at least one electron source is designed such that the electrons strike the anode in a direction that is oriented at least approximately perpendicular to the longitudinal direction of said anode.

To vary the emission characteristic of the x-ray source, there is the desire to be able to adjust the focal spot size of the electron beam on the surface of the anode. According to one embodiment at least one electron source and the anode are therefore movable relative to one another such that the direction in which the emitted electrons strike on the surface of the anode can be displaced in a transversal direction that is oriented both perpendicular to the longitudinal direction and perpendicular to the direction of the electrons. According to a further embodiment an alternative possibility is that the at least one electron source is designed such that this can be displaced in a transversal direction relative to the anode.

According to the two cited embodiments, a variation of the focal spot size can be produced via the adjustment of the electron beam and/or via the displacement of the anode. The size of the focal spot has a direct influence on the physical spatial resolution that can be achieved with the x-ray source. A particularly small focal spot that would enable a high physical spatial resolution has the disadvantage that the anode is very severely thermally loaded. In contrast to this, a large focal spot provides for a low thermal load, wherein the physical spatial resolution turns out to be lower, however. The possibility to vary the focal spot size now affords the user the freedom to set a small focal spot size given lower required x-ray power and thus to achieve a high spatial resolution. In contrast to this, if the x-ray emission power should turn out to be particularly high—wherein the spatial resolution is of less interest—the user has the possibility to increase the focal spot size to protect the x-ray source from thermal overloading.

The x-ray system according to the invention has an x-ray source as described above. In the x-ray system an examination subject is exposed from a plurality of different exposure directions, wherein these are respectively associated with an emission center of the x-ray source. Since the previously explained x-ray source is suitable to generate high emission powers, short exposure times at high resolution and a simultaneously stationary tube can be realized with the x-ray system according to the invention.

DESCRIPTION OF THE PREFERRED EMBODIMENTS

Figure 1:
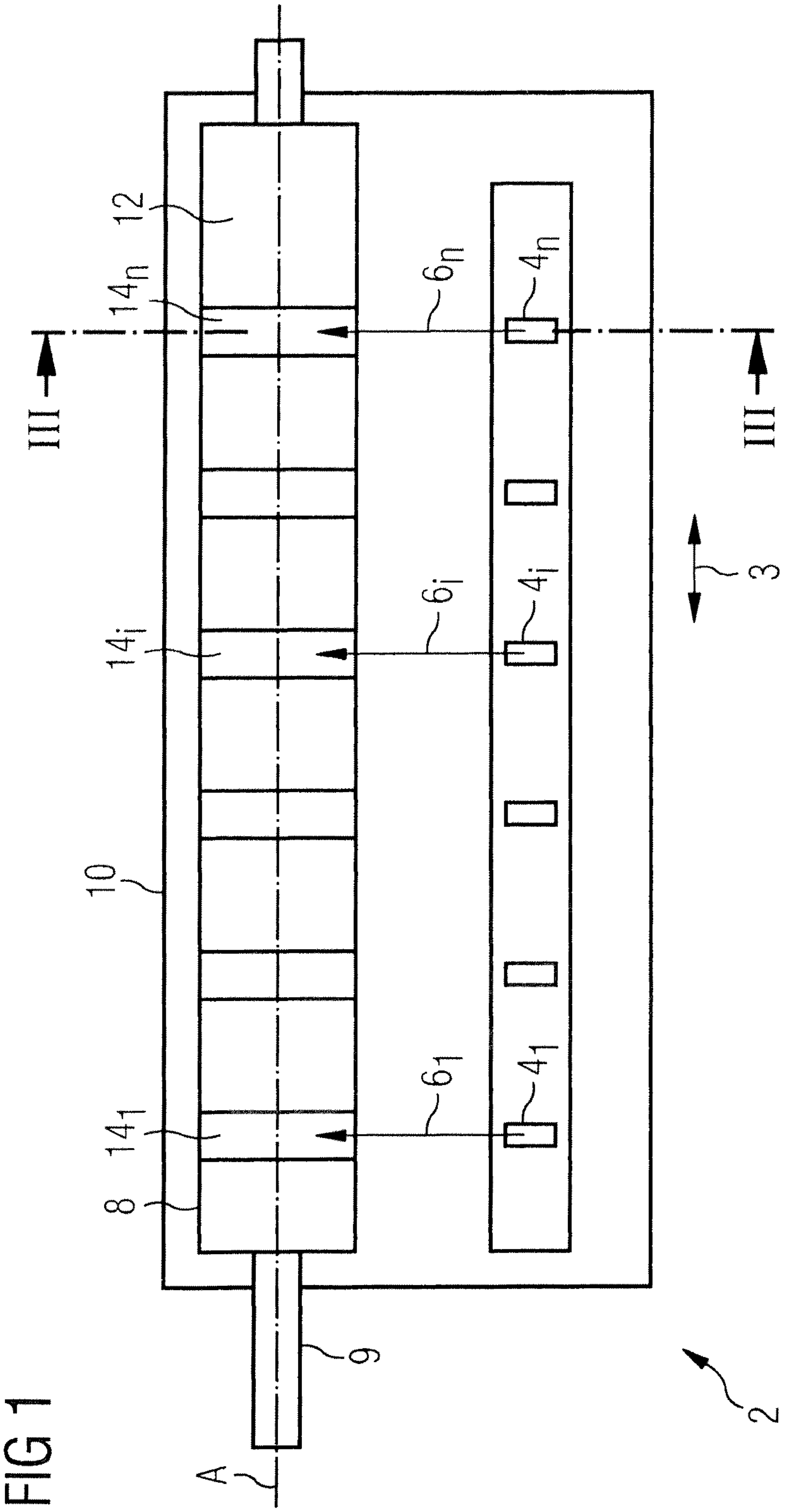
FIG. 1 is a longitudinal view of a first embodiment of an x-ray source in accordance with the present invention.

FIG. 1 shows an x-ray source 2 as it can be used in a mammography system to generate tomosynthetic image data sets, for example. The x-ray source 2 can be used in the same manner for other x-ray systems in which the examination subject is exposed from a plurality of different directions. The x-ray source 2 has a number of electron sources $\mathbf{4}_1$ through $\mathbf{4}_n$ arranged next to one another in the longitudinal direction 3 of the x-ray source 2. Each of the electron sources $\mathbf{4}_1$ through $\mathbf{4}_n$ includes a cathode based on carbon nanotubes; however, conventional filament cathodes can be used in the same manner. Beam shaping components (for example a concentration cup) are not shown for reasons of clarity. The electron sources $\mathbf{4}_1$ through $\mathbf{4}_n$ that are arranged next to one another in the longitudinal direction 3 in the manner of an array can be activated individually so that these each emit an electron beam $\mathbf{6}_1 \ldots \mathbf{6}_n$ individually or in groups, which electron beam $\mathbf{6}_1 \ldots \mathbf{6}_n$ is directed toward the surface of the anode 8 rotating in the operation of the x-ray source 2. Via a shaft 9 the essentially cylindrical anode 8 is mounted in the housing 10 of the x-ray source 2 such that it can rotate around an axis A.

The anode 8 is a composite anode made of a base body 12 and a cover layer that is formed from a plurality of segments $\mathbf{14}_1$ through $\mathbf{14}_n$ that are spaced apart from one another in the longitudinal direction 3. Every electron source $\mathbf{4}_1$ through $\mathbf{4}_n$ is associated with a segment $\mathbf{14}_1$ through $\mathbf{14}_n$ situated opposite it. An electron beam $\mathbf{6}_1$ emanating from the electron source $\mathbf{4}_1$ is thus directed towards the segment $\mathbf{14}_1$.

The material of the segments $\mathbf{14}_1$ through $\mathbf{14}_n$ determines the type of x-ray emission of the x-ray source 2. In the exemplary embodiment shown in FIG. 1, the segments $\mathbf{14}_1$ through $\mathbf{14}_n$ of the cover layer are made of molybdenum.

The x-ray source 2 is suitable to emit n x-ray beams simultaneously or in succession, corresponding to the number of its electron sources $\mathbf{4}_1$ through $\mathbf{4}_n$ and segments $\mathbf{14}_1$ through $\mathbf{14}_n$. This occurs by corresponding activation of the electron sources $\mathbf{4}_1$ through $\mathbf{4}_n$. The emission centers that are generated by the electrons striking the segments $\mathbf{14}_1 \ldots \mathbf{14}_n$ are themselves spaced apart from one another in the longitudinal direction 3 corresponding to the segments $\mathbf{14}_1 \ldots \mathbf{14}_n$. The x-ray source 2 is consequently suitable to emit x-ray beams that come from different directions. Since the anode 8 rotates around the axis A during the operation of the x-ray source 2, a focal spot path that is heated by the respective electron beam $\mathbf{6}_1$ through $\mathbf{6}_n$ is formed along the segments $\mathbf{14}_1$ through $\mathbf{14}_n$ in the circumferential direction of the anode 8. The width of the segments $\mathbf{14}_1$ through $\mathbf{14}_n$ is advantageously selected precisely so that this essentially corresponds to the width of the focal spot path. The heat introduced into the anode 8 is predominantly emitted again in the form of radiation. However, it is likewise conceivable that cooling channels run through the inside of the anode 8, such that this can be actively cooled by a coolant which (for example) is supplied via the axis 9 of the anode 8.

The base body 12 and the segments $\mathbf{14}_1$ through $\mathbf{14}_n$ are produced from different materials. While the material of the segments $\mathbf{14}_1$ through $\mathbf{14}_n$ determines the type of x-ray emission of the x-ray source 2, the base body 12 serves primarily to discharge the heat introduced into the segments $\mathbf{14}_1$ through $\mathbf{14}_n$ by the electron beams $\mathbf{6}_1$ through $\mathbf{6}_n$. For this reason the segments $\mathbf{14}_1$ through $\mathbf{14}_n$ are recessed into the surface of the base body 12, which is produced from graphite due to its good thermal conductivity. The segments $\mathbf{14}_1$ through $\mathbf{14}_n$ that take up a portion of the surface shell of the base body 12 extend along the circumference of the base body 12 and are advantageously fashioned in the form of hoops or, respectively, rings.

The emission of the x-ray source 2 is dependent on the material of the segments, which has the same function and task as the material of the anode in conventional x-ray sources. For this reason the material of the segments $\mathbf{14}_1$ through $\mathbf{14}_n$ is also designated as anode material.

Figure 2:
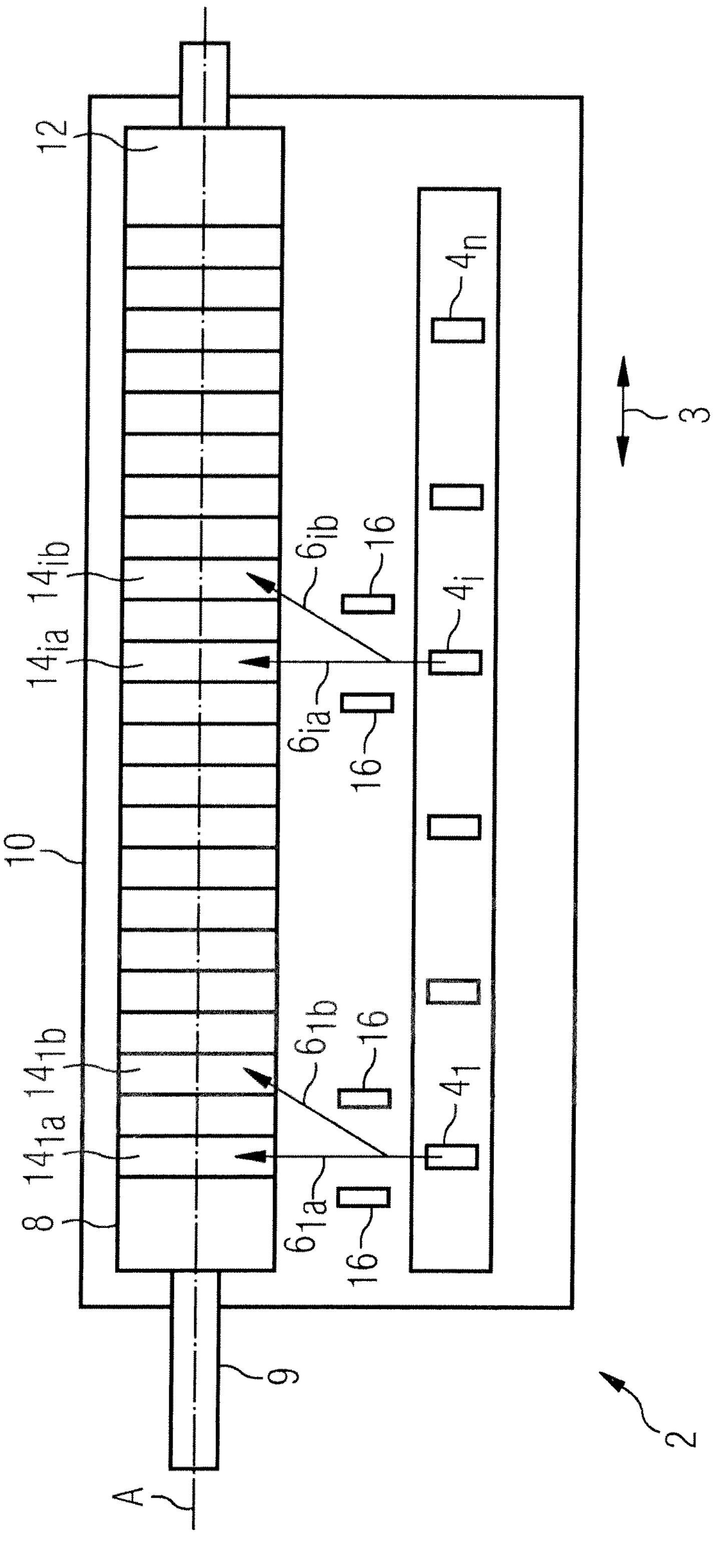
FIG. 2 is a longitudinal view of a second embodiment of the x-ray source in accordance with the present invention.

FIG. 2 shows another embodiment of the x-ray source 2, which has two different anode materials. The x-ray source 2 is suitable for the emission of two different x-ray spectra (or of two different x-ray emissions in general).

The anode 8 has segments $\mathbf{14}_{1a}$, $\mathbf{14}_{1b}$ through $\mathbf{14}_{na}$, $\mathbf{14}_{nb}$ that are subdivided into two segment groups with the indices a and b. The segments $\mathbf{14}_{1a}$ through $\mathbf{14}_{na}$ of the segment group a are made of molybdenum while the segments $\mathbf{14}_{1b}$ through $\mathbf{14}_{nb}$ of the segment group b are made of tungsten. The segments $\mathbf{14}_{1a}$, $\mathbf{14}_{1b}$ through $\mathbf{14}_{na}$, $\mathbf{14}_{nb}$ are composed in pairs; two segments $\mathbf{14}_{ia}$, $\mathbf{14}_{ib}$ are associated with an electron source $\mathbf{4}_i$.

To generate different x-ray emissions, with the use of the deflection coils 16 the electron beam $\mathbf{6}_i$ emanating from the x-ray source 5, is selectively directed as electron beam $\mathbf{6}_{ia}$ towards the molybdenum segment $\mathbf{14}_{ia}$ or as electron beam $\mathbf{6}_{ib}$ toward the tungsten segment $\mathbf{14}_{ib}$. It is now possible to direct the electron beams $\mathbf{6}_1$ through $\mathbf{6}_n$ of all electron sources $\mathbf{4}_1$ through $\mathbf{4}_n$ toward either the molybdenum segments $\mathbf{14}_{1a}$ through $\mathbf{14}_{na}$ or towards the tungsten segments $\mathbf{14}_{1b}$ through $\mathbf{14}_{nb}$. In this case the x-ray emission of the entire x-ray source 2 would be switched back and forth. However, it is likewise possible to specifically switch only individual electron sources of the electron sources $\mathbf{4}_1$ through $\mathbf{4}_n$ so an x-ray source 2 with mixed mission characteristic is created.

As described, a changing of the x-ray emission can ensue via a deflection of the electron beams $\mathbf{6}_1$ through $\mathbf{6}_n$ with the aid of deflection coils 16. Alternatively, the anode 8 can be displaced by a corresponding amount in the longitudinal direction 3 so that as a consequence of the displacement the electron beams $\mathbf{6}_1$ through $\mathbf{6}_n$ now strike the tungsten segments $\mathbf{14}_{1b}$ through $\mathbf{14}_{nb}$, for example, instead of striking the molybdenum segments $\mathbf{14}_{ia}$ through $\mathbf{14}_{na}$ that were originally struck.

Figure 3:
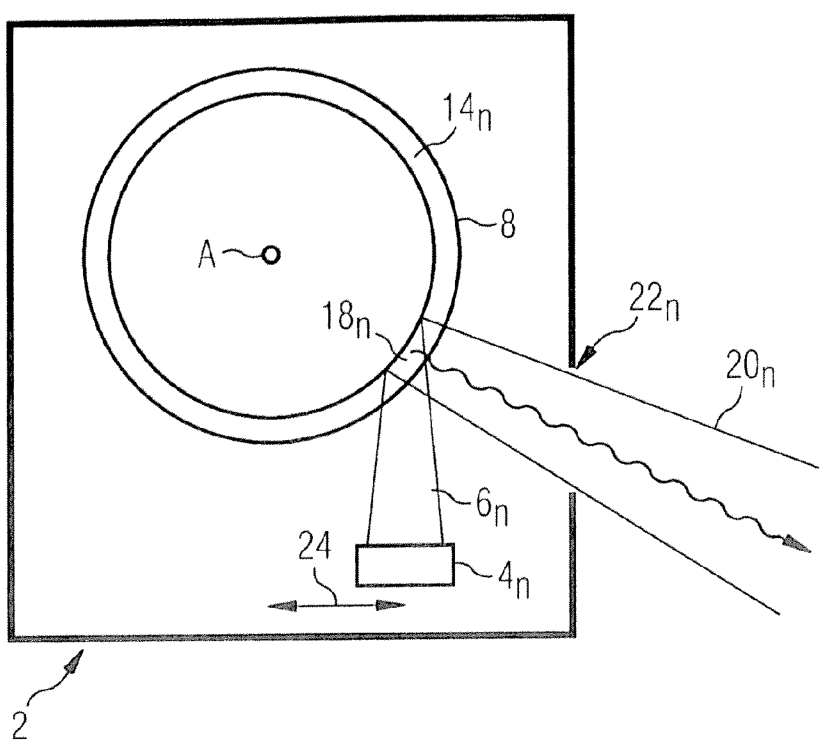
FIG. 3 is a sectional view of the first embodiment of the x-ray source shown in FIG. 1, taken along line III-III.

FIG. 3 shows a cross section view of the x-ray source 2 shown in FIG. 1 along the slice plane designated with III-III. The electron beam $\mathbf{6}_n$ emanating from the electron source $\mathbf{4}_n$ strikes the anode 8 (which rotates around the axis A within the housing 10) in the region of the segment $\mathbf{14}_n$. Due to the electron bombardment an emission center 18, is caused within the anode material of the segment $\mathbf{14}_n$. This is typically also designated as a focal spot. The x-ray beam $\mathbf{20}_n$ that emanates from the emission center $\mathbf{18}_n$ leaves the material of the segment $\mathbf{14}_n$ and is delimited by the window $\mathbf{22}_n$. The x-ray beam 20, emanating from the emission center $\mathbf{18}_n$ can moreover be delimited by additional optical components (for example collimator diaphragms; not shown) besides the window $\mathbf{23}_n$ shown in FIG. 3. The emission characteristic of the x-ray source 2 can be varied by a displacement of the electron source $\mathbf{4}_n$ in the transversal direction 24 that is oriented essentially perpendicular to the axis A or, respectively, to the longitudinal direction 3 (not shown in FIG. 3). The transversal direction 24 is moreover oriented essentially perpendicular to the direction of the electron beam $6_n$ that is emitted by the electron source $4_n$.

Figure 4:
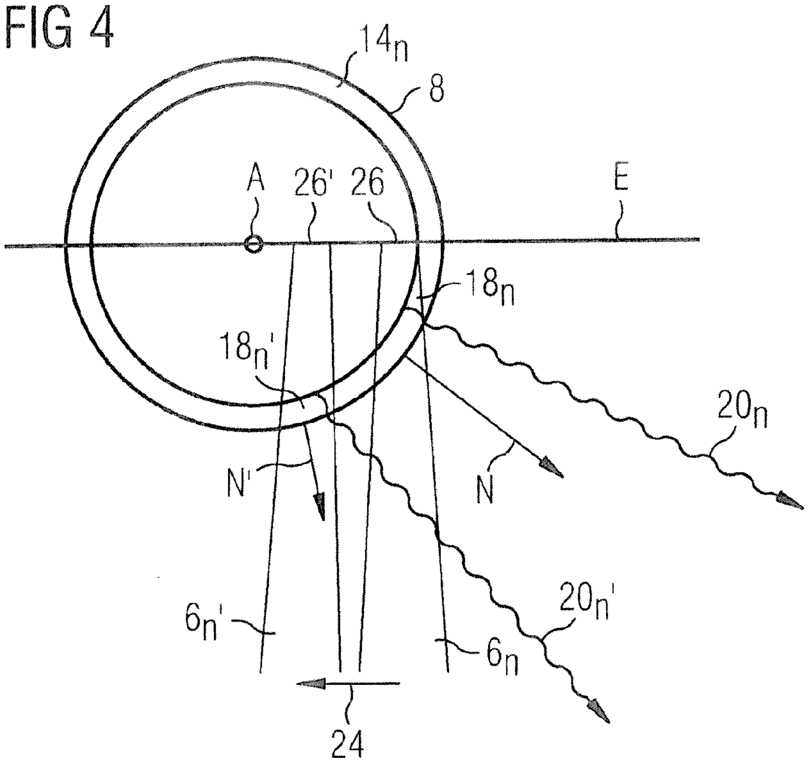
FIG. 4 shows the anode of the x-ray source in accordance with the present invention, in cross-section.

FIG. 4 shows a detailed view of the x-ray source 2 presented in FIG. 3, wherein the electron source $4_n$ is presented both in its position as shown in FIG. 3 and also as electron source 4*n*' in a position displaced in the transversal direction 24. Corresponding to this displacement, the electron beam $6_n$ now strikes the surface of the anode 8 at a different angle as electron beam $6_n$'.

In the following the radiation direction of the two electron beams $6_n$, $6_n$' before and after the displacement of the electron source $4_n$ is considered relative to the surface perpendiculars N or, respectively, N' of the anode 8. After a displacement in the transversal direction 24, the electron beam $6_n$' strikes the surface of the anode 8 in a region that is situated closer to its rotation axis A. The angle between the radiation direction of the electron beam $6_n$ and the surface perpendicular N before the displacement is greater than the angle between electron beam $6_n$' and the surface perpendicular N' after its displacement. The position of the emission center or, respectively, focal spot $18_n$ varies as a result of the displacement of the electron beam $6_n$.

If the electron beam $6_n$' strikes the anode 8 at the surface close to the axis, meaning that the angle between the impact direction of the electron beam $6_n$' and the surface perpendicular N' of the anode 8 is small, a short focal spot $18_n$' is created. In contrast to this, if the electron beam $6_n$ strikes the anode 8 far from the axis, meaning that the angle between its impact direction and the surface perpendicular N is large, a focal spot $18_n$ is created that is extended in length in the circumferential direction of the anode 8. A short focal spot $18_n$' enables a high physical spatial resolution but likewise leads to a high thermal load of the anode material in the form of the segment $14_n$. A larger focal spot $18_n$ ensures that the thermal energy of the electrons of the striking electron beam $6_n$ that are braked in the anode material is distributed in a larger volume of the anode 8. This leads to the situation that the thermal load of the anode 8 decreases at the cost of a lower physical spatial resolution.

The displacement of the electron beam $6_n$, $6_n$' in the transversal direction 24 can likewise be described as follows: a plane E that contains the rotation axis A and is oriented essentially perpendicular to the electron beams $6_n$, $6_n$' is introduced merely for clarification. Intersection points 26, 26' are constructed by extending the directions of the electron beams $6_n$, $6_n$' into the plane E. The intersection points 26, 26' situated in the plane always lie between the outer edge of the anode 8 and its axis A. As a result of a displacement in the transversal direction 24, the intersection point 26, 26' selectively wanders into a region close to the axis or into a region near the edge of the anode 8.

The x-ray source 2 can be used in x-ray apparatuses in which an examination subject is exposed from different directions. Examples of such x-ray apparatuses from the field of medical technology are: mammography apparatuses, computed tomography apparatuses (CT) or apparatuses for rotation angiography.

Figure 5:
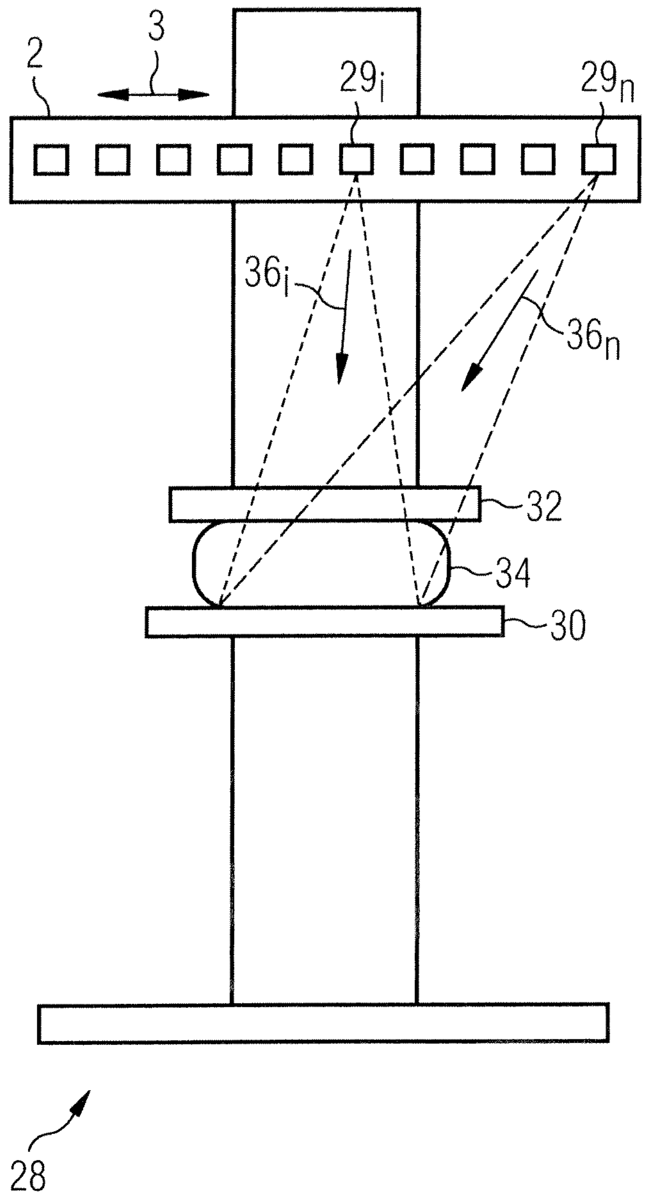
FIG. 5 schematically illustrates a mammography system embodying an x-ray source in accordance with the present invention.

In the following the use of an x-ray source 2 is explained using, for example, the mammography system 28 shown in FIG. 5. This possesses an x-ray source 2 as it is shown in FIG. 1. The x-ray source 2 has schematically depicted x-ray emitters $29_1$ through $29_n$ that extend in the longitudinal direction 3 of the x-ray source 2. Each x-ray emitter 29, . . . , $29_n$ has at least one electron source 4 and the segment 14 of the anode 8 that is associated with the electron source 4. In that different x-ray emitters $29_1$ through $29_n$ of the x-ray source 2 are excited to emission, the breast 34 that is located between a detector 30 and a compression plate 32 can be irradiated from different exposure directions $36_1$ through $36_n$. For example, for this purpose the individual x-ray emitters $29_1$ through $29_n$ are excited to emission in chronological order. For example, if the emission center $29_i$ is excited to emission, the breast 34 is irradiated from the direction 36*i*. If the emission center $29_n$ is excited to emission, the breast 34 is exposed from the direction $36_n$. A mammography system 28 as FIG. 5 shows is suitable for the acquisition of tomosynthesis image data sets.

Although modifications and changes may be suggested by those skilled in the art, it is the intention of the inventors to embody within the patent warranted heron all changes and modifications as reasonably and properly come within the scope of their contribution to the art.

We claim as our invention:

1. An x-ray source comprising:

a housing;

a plurality of electron sources in said housing, said electron sources being spaced apart from each other along a longitudinal direction;

a single anode operable in common with all of said electron sources, said anode being mounted in said housing for rotation around a rotation axis that is parallel to and defines said longitudinal direction;

said anode body being a composite comprising a base body and a cover layer over said base body, said cover layer being comprised of anode material that interacts with said electrons to emit x-rays, said base body and said cover layer being respectively comprised of different material compositions;

said cover layer being subdivided into a plurality of segments each proceeding around a periphery of said anode body, said segments being spatially spaced apart from each other along said longitudinal direction each having respective emission spectrum; and each of said electron source emitting electrons that strike only a location in a respective one of said segments on said anode that are spatially separated from each other along said longitudinal direction, the respective locations forming separate emission centers, each emission center being individually associated with one of said electron sources, and each emission center emitting x-rays with an emission spectrum defined by the segment, among said plurality of segments, in which that emission center is located.

2. An x-ray source as claimed in claim 1 wherein said anode body is rotationally symmetric with respect to said rotation axis.

3. An x-ray source as claimed in claim 1 wherein said cover layer is recessed into said base body.

4. An x-ray source as claimed in claim 1 wherein said segments are grouped to form a first segment group and a second segment group, with segments in said first second group alternating with segments in said second segment group on said anode body along said longitudinal direction, with the segments in said first segment group having a material composition that is different from the segments in said second segment group.

5. An x-ray source as claimed in claim 4 wherein said segments in said first segment group consist essentially of molybdenum, and the segments in said second group consist essentially of tungsten.

6. An x-ray source as claimed in claim 1 wherein said base body essentially consists of graphite.

7. An x-ray source as claimed in claim 1 wherein said anode is cylindrical and wherein at least one of said electron sources is positioned relative to said anode to cause electrons emanating from said one of said electron sources to strike a surface of said anode at one of the strike points from a direction that differs from a surface normal of the anode at said one of said strike points.

8. An x-ray source as claimed in claim 7 wherein said at least one of said electron sources is positioned to cause said electrons therefrom to strike said surface of said anode at said one of said strike points at a direction oriented substantially perpendicularly to said longitudinal direction.

9. An x-ray source as claimed in claim 8 wherein said at least one electron source and said anode are mounted in said housing to be movable relative to each other to allow transverse displacement of the direction at which electrons from said at least one of said electron sources strikes said anode surface, along a transverse direction that is perpendicular to both said longitudinal direction and to said direction of said electrons.

10. An x-ray source as claimed in claim 9 wherein said at least one electron source is displaceable relative to said anode along said transverse direction.

11. An x-ray source as claimed in claim 1 wherein at least one of said electron sources comprises a carbon nanotube catheter.

12. A mammography system comprising:

an x-ray source comprising a housing, a plurality of electron sources in said housing, said electron sources being spaced apart from each other along a longitudinal direction, a single anode operable in common with all of said electron sources, said anode being mounted in said housing for rotation around a rotation axis that is parallel to and defines said longitudinal direction, said anode body being a composite comprising a base body and a cover layer over said base body, said cover layer being comprised of anode material that interacts with said electrons to emit x-rays, said base body and said cover layer being respectively comprised of different material compositions, said cover layer being subdivided into a plurality of segments each proceeding around a periphery of said anode body, said segments being spatially spaced apart from each other along said longitudinal direction each having respective emission spectrum, and each of said electron source emitting electrons that strike only a location in a respective one of said segments on said anode that are spatially separated from each other along said longitudinal direction, the respective locations forming separate emission centers, each emission center being individually associated with one of said electron sources, and each emission center emitting x-rays with an emission spectrum defined by the segment, among said plurality of segments, in which that emission center is located;

a radiation detector that detects x-rays;

a stand on which said x-ray source and said radiation detector are mounted allowing a subject to be placed therebetween so that said x-ray detector detects x-rays from said x-ray source that are attenuated by said subject; and a control unit that operates said x-ray source to acquire a tomosynthesis image data set.

13. An x-ray system comprising:

an x-ray source comprising a housing, a plurality of electron sources in said housing, said electron sources being spaced apart from each other along a longitudinal direction, a single anode operable in common with all of said electron sources, said anode being mounted in said housing for rotation around a rotation axis that is parallel to and defines said longitudinal direction, said anode body being a composite comprising a base body and a cover layer over said base body, said cover layer being comprised of anode material that interacts with said electrons to emit x-rays, said base body and said cover layer being respectively comprised of different material compositions, said cover layer being subdivided into a plurality of segments each proceeding around a periphery of said anode body, said segments being spatially spaced apart from each other along said longitudinal direction each having respective emission spectrum, and each of said electron source emitting electrons that strike only a location in a respective one of said segments on said anode that are spatially separated from each other along said longitudinal direction, the respective locations forming separate emission centers, each emission center being individually associated with one of said electron sources, and each emission center emitting x-rays with an emission spectrum defined by the segment, among said plurality of segments, in which that emission center is located;

a radiation detector that detects x-rays;

a stand on which said x-ray source and said radiation detector are mounted allowing a subject to be placed therebetween so that said x-ray detector detects x-rays from said x-ray source that are attenuated by said subject; and a control unit that operates said x-ray source to selectively activate said plurality of electron sources to expose said subject to x-rays from respectively different exposure directions, each exposure direction being respectively associated with one of said emission centers of said x-ray source.

* * * * *